United States Patent [19]

Takahashi et al.

[11] 4,085,274

[45] Apr. 18, 1978

[54] PROCESS FOR PREPARING 4-OXOPENTADECANEDIOIC ACID

[75] Inventors: Katuhiko Takahashi; Kyozo Arimoto; Yoshiyuki Arai; Tsuyoshi Morinaga; Yuji Nakazawa, all of Ohimachi, Japan

[73] Assignee: Daicel Ltd., Sakai, Japan

[21] Appl. No.: 690,360

[22] Filed: May 26, 1976

[30] Foreign Application Priority Data

May 30, 1975 Japan .................. 50-65014

[51] Int. Cl.² ............... C07C 51/34; C07C 67/00
[52] U.S. Cl. .................. 560/176; 260/396 R; 260/514 K; 260/533 D; 260/537 R; 260/343.21; 560/127
[58] Field of Search ........... 260/468, 514, 483, 537 R, 260/533 D

[56] References Cited

U.S. PATENT DOCUMENTS 3,383,398  5/1968  Peck et al. ................ 260/413
3,414,594  12/1968  Dubeck et al. ............. 260/413

OTHER PUBLICATIONS

House, Modern Synthetic Reactions, pp. 664–665, (1972).
March, Advanced Organic Chemistry, pp. 478–479, 870–874, (1969).
Fiesen et al., Reagents for Organic Synthesis, pp. 774–777, 1244, (1967).

Primary Examiner—Robert Gerstl
Attorney, Agent, or Firm—Blanchard, Flynn, Thiel, Boutell & Tanis

[57] ABSTRACT 4-oxopentadecanedioic acid is prepared by oxidizing a α-cyclododec-1-enylpropionic acid derivative having one of the following chemical formulae at its ethylenic double bond with ozone.

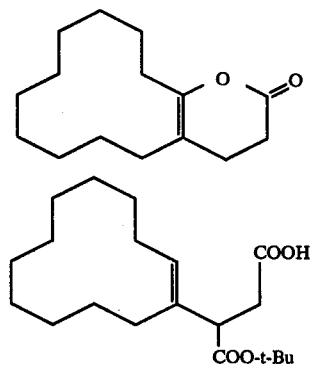

The compound is useful as an intermediate for a musk perfume compound. The compound having the formula II is selectively prepared from cyclododecanone and di-alkyl succinate.

2 Claims, 3 Drawing Figures

PROCESS FOR PREPARING 4-OXOPENTADECANEDIOIC ACID

BACKGROUND OF THE INVENTION

1. Field of the Invention

This invention relates to a novel process for preparing 4-oxopentadecanedionic acid, useful as an intermediate for musk perfume compounds such as cyclopentadecanone VI and cyclopentadecanolide VI-L. These musk perfume compounds have a similar macrocyclic structure as natural musk perfume compounds.

2. Description of Prior Arts

There have been known various processes for obtaining a macrocyclic musk perfume compound. But they have disadvantages: Some of them give only a low yield: some employ poisonous heavy metal compounds such as manganese and lead; some employ Grignard agents which will cause safety troubles; some employ starting materials which are not available with ease. Among conventional processes, there is an interesting process in which cyclopentadecanone VI is prepared by acyloin condensation and reduction of dimethyl pentadecanedioate V (Yonetani et al: The KORYO, No. 48, p 22–25, 1958). Dimethyl pentadecanedioate V can be obtained by reducing 4-oxopentadecanedioic acid IV, which is the object of this invention and will be hereinafter referred to as ketodicarboxylic acid, with hydrazine hydrate in the presence of potassium hydroxide and then esterifying the resulting product. The compound VI is also obtainable by acyloin condensation and reduction of the compound IV after the protection of its carbonyl group by forming a ketal.

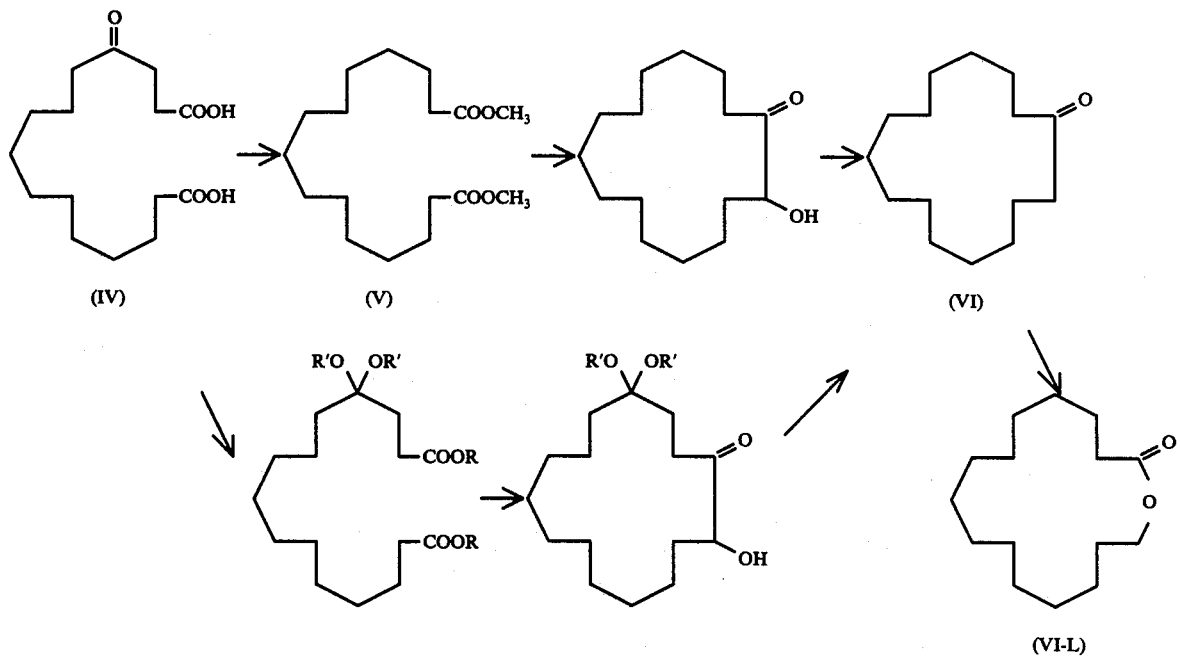

As to a process for preparing 4-oxopentadecanedioic acid by oxidation and cleavage of the ethylenic unsaturated bond of a cyclic compound, Japanese patent publication 21690/70 discloses oxidation of bicycloketone VII. Bicycloketone is prepared from cyclododecanone VIII through three steps with the total yield of about 63 percent (Japanese patent publication 4341/69). Since 4-oxopentadecanedioic acid is obtained by ozone oxidation of bicycloketone VII with a yield of 63 to 77 percent, the yield of 4-oxopentadecanedioic acid from cyclododecanone VIII will be 40 to 49 percent.

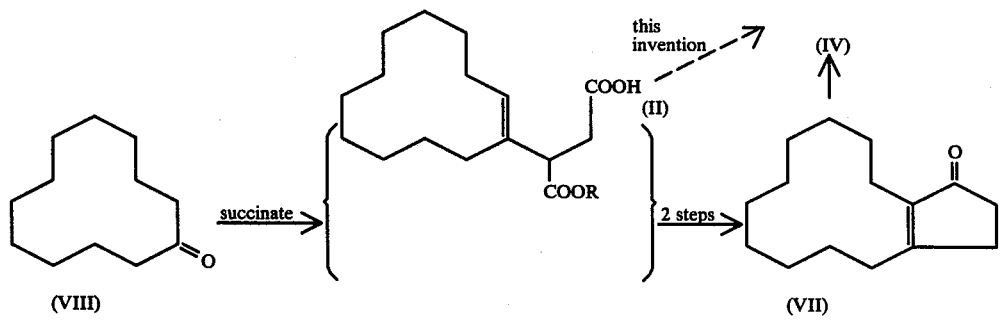

-continued

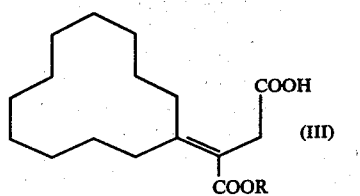
(III)

As to the first step in which cyclododecanone VIII is converted to bicycloketone VII, there is known a process for preparing an unsaturated bicarboxylic acid half ester by the Stobbe condensation reaction between cyclododecanone and succinic acid diester such as diethyl succinate. As disclosed in Japanese patent publication 4341/69, the unsaturated half ester is obtained with two chemical structures, namely, the alkylidene type III and the alkenyl type II. The proportion of these two isomers is referred to in Biemann et al: J. Am. Chem. Soc., 79, 5558 (1957), in which the product of the alkylidene type was identified with UV spectrum. When the product, diethyl succinate is employed, the product III will be the main product U.S. Pat. No. 3,778,483 discloses a process for preparing the product of the alkenyl type from cyclododecanone and dimethyl or diethyl succinate, referred to as method B. But according to that patent, it is merely taught that bicycloketone is prepared by treatment with polyphosphoric acid, but it is not taught in detail that that of alkenyl type is selectively obtained.

SUMMARY OF INVENTION

This invention relates to a novel preparation of 4-oxopentadecanedioic acid. The primary object of this invention is to select a cyclic compound having an ethylenic unsaturated bond in order to prepare 4-oxopentadecanedioic acid with a high efficiency by oxidation, whereby a useful intermediate for cyclopentadecanone which is a musk perfume compound, is effectively obtained from cyclododecanone which is widely available. The second object of this invention is to provide a process for selectively preparing β-cyclododec-1-enyl-β-alkoxy carbonyl propionic acid which is one of the unsaturated cyclic compounds to be used in the above mentioned process. To obtain 4-oxopentadecanedioic acid by ozone oxidation of the Stobbe condensation product, the unsaturated half ester is required to have the alkenyl type structure. In a conventional process in which the diethyl ester is employed, a mixture of the both half esters is converted to alkenyl type bicycloketone by treatment with polyphosphoic acid in order to attain a selective synthesis. The further object of this invention is to avoid employment of a large amount of polyphosphoric acid and to obtain the alkenyl type half ester with ease, which can be subjected to subsequent oxidation. The process of this invention is very simple.

The first object of this invention can be attained by oxidizing a cyclododec-1-enyl propionic acid derivative with ozone and then decomposing the resulting product, followed by recovery of the final product.

The second object can be attained by employment of a dialkyl succinate in the reaction between cyclododecanone and the dialkyl succinate.

The third object can be attained by a combination of the above mentioned process to attain the first object and the process to attain the second or another invention by the present inventors, titled to "13-oxabicylo [10.4.0] hexadec-1(12) en-14-one and its preparation" (U.S. Patent application, Ser. No. 629,391, now Pat. No. 4,005,107).

As above mentioned, 4-oxopentadecanedioic acid is prepared from cyclododecanone with a high yield and with simplicity. This product is an intermediate for cyclopentadecanone, which is a musk perfume compound.

DETAILED DESCRIPTION OF INVENTION

Figure 1:
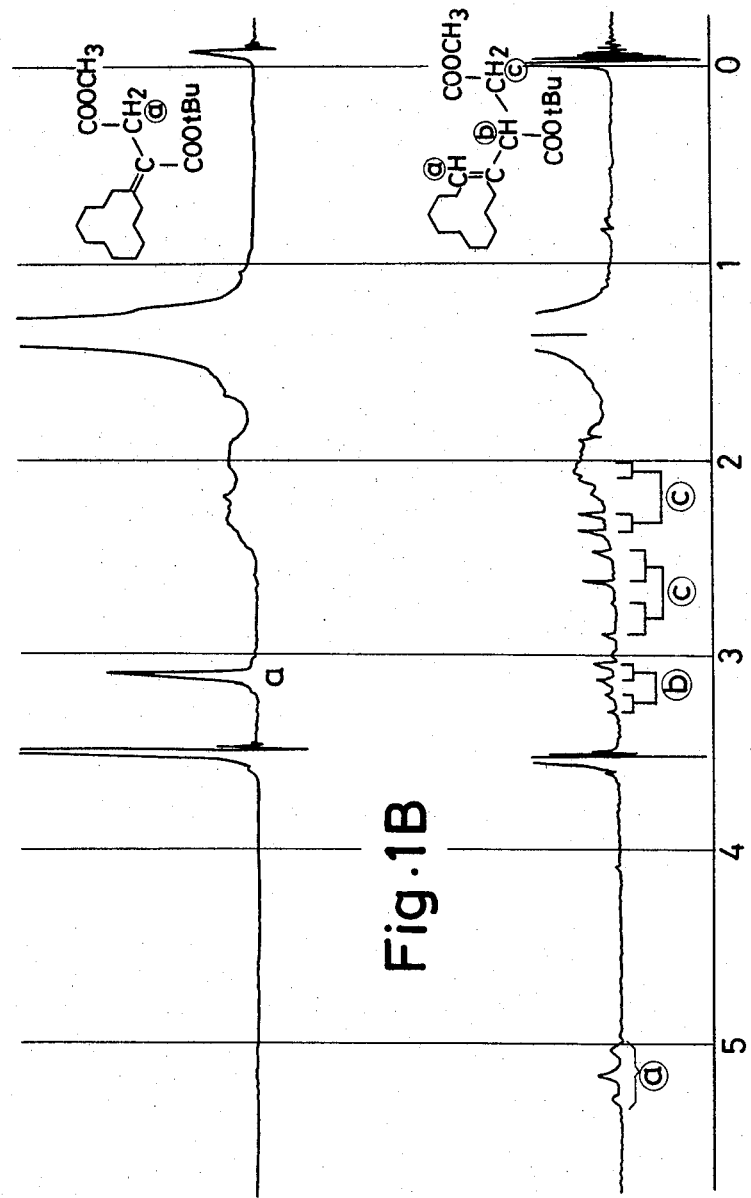
FIG. 1 shows the NMR spectrum of the compound obtained in Example 5 and FIG. 2 shows Gas Chromatogram thereof.

A cyclododec-1-enyl propionic acid derivative to be used in this invention has the following general formula:

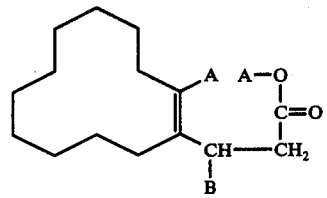

in which A is an atomic bond and B is hydrogen or A is hydrogen and B is an alkoxycarbonyl group, and includes the following two compounds.

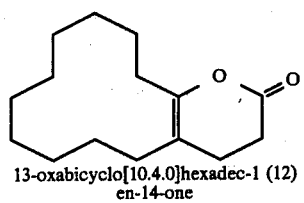

13-oxabicyclo[10.4.0]hexadec-1 (12) en-14-one

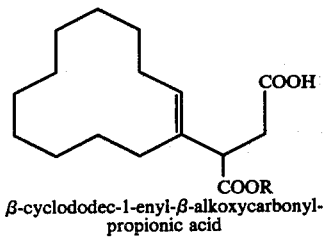

β-cyclododec-1-enyl-β-alkoxycarbonyl-propionic acid

The compound I is obtained by the method disclosed in U.S. Patent application Ser. No. 629,391 now Pat. No. 4,005,107 by the present inventors, which relates to cyclization of β-(2-oxocyclododecyl)propionic acid IX or its derivative. The compound IX is obtained by methods employing cyclododecanone VIII as the starting material.

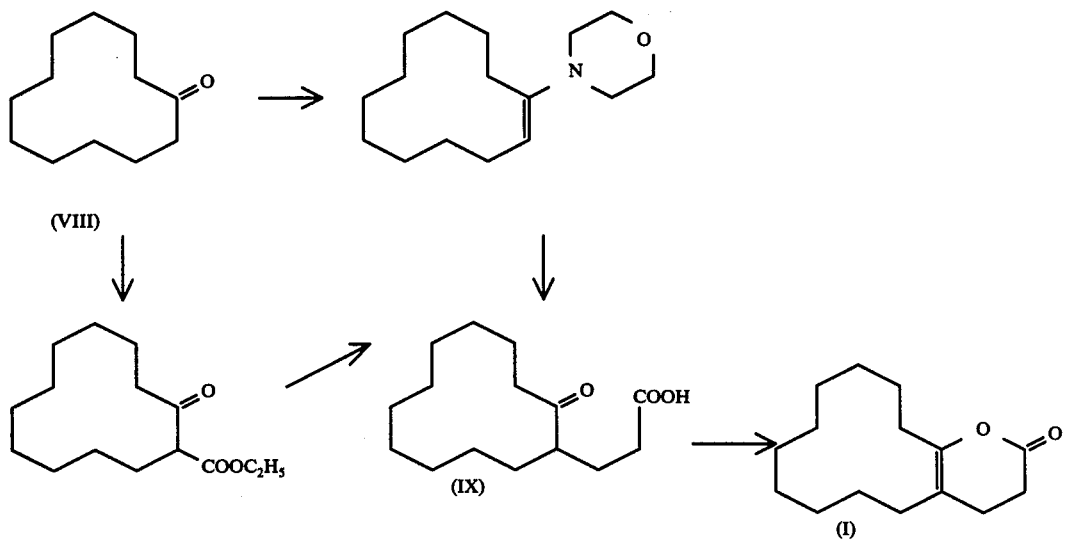

The compound II is obtained by Stobbe condensation between cyclododecanone and succinic acid diester. This method will be illustrated later.

According to this invention, oxygen gas or air containing ozone is introduced into a solution of the compound I or II to produce an oxidation product, which is then decomposed and the resulting product is separated as 4-oxopentadecanedioic acid IV or its ester. The oxidation of bicyclo [10.3.0] pentadecl (12)-en-13-one (2,3-decamethylene-2-cyclopentenone) VII, as is disclosed in Japanese patent publication 21690/70, comprises oxidizing the cyclic compound at its ethylenic unsaturated bond to cause cleavage of bond and is accordingly considered to be very close to this invention. However the starting material to be used in that process is bicycloketone which is obtained with employment of a large amount of polyphosphoric acid, as described in Japanese patent publication 4341/69.

This invention differs from that process in this regard, because it requires as the starting material a propionic acid derivative which is industrially available with ease. This is the reason why this invention does not have such a disadvantage.

In ozone oxidation, as a solvent there is used hydrocarbons, halogenated hydrocarbons, alcohols, fatty acids and others. Halogenated hydrocarbons such as dichloromethane, chloroform and carbon tetrachloride are preferred with regard to solubility of the starting materials and the products and inertness to the reactants. In addition, there may be used a solvent mixture of a halogenated hydrocarbon and a fatty acid such as acetic acid, which provides ozone oxidation of an compound II with the improved result, compared with employment of a halogenated hydrocarbon alone. The reaction temperature of ozone oxidation may range from $-80°$ C to room temperature, and preferably from $-30°$ C to $0°$ C. Ozone is blown into the reaction system in the form of a mixture with oxygen or air; and the molar amount is equal to the number of moles of ethylenic unsaturated bond of the compound I or II or a little excess. The end point of the reaction will occur when the reaction mixture is colored blue by dissolved ozone. The reaction can be usually conducted under atmospheric pressure, but the pressure is not limited thereto.

The product oxidized with ozone does not need to be separated. It is subsequently decomposed in the reaction mixture to obtain a ketodicarboxylic acid. Although the product oxidized with ozone does not necessarily comprise a single substance, the process of the present invention will be represented by the following reaction scheme.

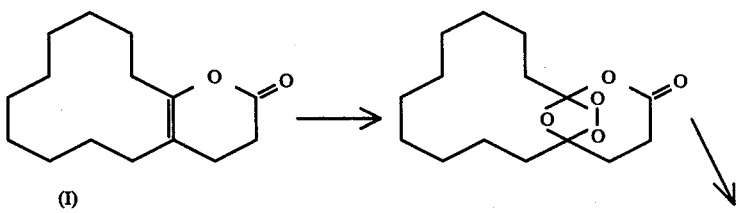

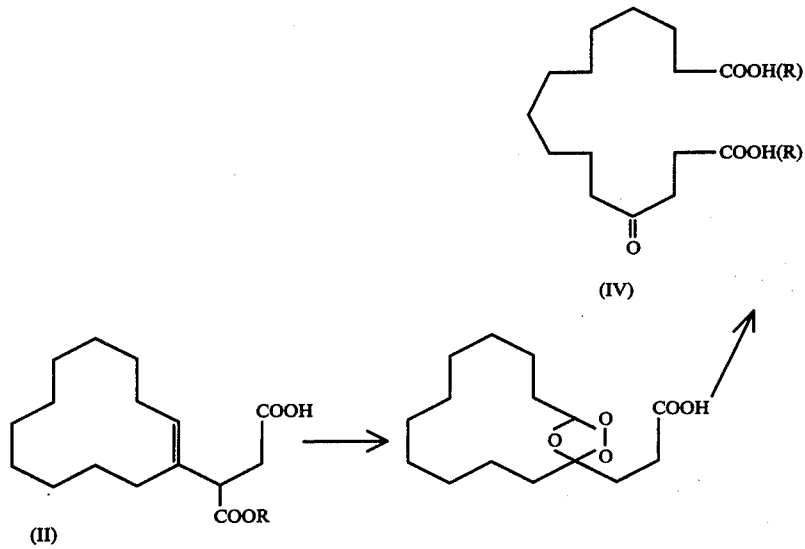

Below is described in detail the decomposition of the ozone-oxidized product of the compound I.

The term "decomposition" used in the present invention includes the reductive or oxidative cleavage of the ozone-oxidized product, and subsequent hydrolysis with an alkali aqueous solution, decomposition of the ozone-oxidized product with a basic aqueous solution and the decomposition of ozone-oxidized product with an alcohol containing an acid catalyst, as illustrated below.

(1) Reductive cleavage and subsequent hydrolysis:

General reducing agents may be used as a cleaving agent. But in view of the reaction operation, it is preferred to use an organic reducing agent that dissolves in a solvent which is used at the time of oxidation with ozone. Examples are sulfides such as dimethyl sulfide and phosphines such as triphenyl phosphine. Inorganic reducing agents such as sodium sulfite aqueous solutions that are often used as a reducing agents of ozonides, on the other hand, are not efficient even if used alone or even if admixed with methanol, due to their limited compatibility. The catalytic reduction using molecular hydrogen and a metal catalyst, involves also problems of conducting the reaction on an industrial scale, because it is accompanied by the danger of explosion. The cleavage proceeds quickly over the temperature range of −30° C to room temperature. After the reduction, the compound is condensed and heated being admixed with an alkali aqueous solution to obtain the ketodicarboxylic acid IV in the form of an alkali salt. The free acid can be obtained from the above salt by a customary method.

(2) Oxidative cleavage and subsequent hydrolysis:

Like the reductive cleavage method, the solubility of the cleavage agent in the reaction system must greatly affects the reaction results. That is, the effective cleavage agents are organic peracid such as peracetic acid, perbenzoic acid, perphthalic acid, and m-chloroperbenzoic acid. Hydrogen peroxide used alone does not exhibit too much efficiency, but serves to heighten the reaction results if used in combination with an organic acid such as formic acid or acetic acid. The cleavage proceeds even if the system is left to stand at room temperature, but proceeds more quickly if the system is heated at the refluxing temperature of the solvent. After the oxidative cleavage, the compound is condensed and heated being admixed with an alkali aqueous solution to obtain the ketodicarboxylic acid IV in the form of an alkali salt. Free acid can be obtained from the alkali salt by a customary manner.

(3) Decomposition with a basic aqueous solution:

There are other decomposing agents that can decompose the ozone-oxidized product of the compound I to a ketodicarboxylic acid IV. For example, when the oxidation with ozone is finished, the addition of an aqueous sodium hydroxide solution causes violent reaction; with this method, however, it is difficult to control the reaction, and the yield of the object ketodicarboxylic acid is small. Astonishingly, however, it is possible to prepare a ketodicarboxylic acid in very good yield by adding a basic aqueous solution including a base, a water-soluble organic compound and water to the ozone-oxidation reaction liquid at −30° C to 0° C, returning the reaction temperature gradually back to room temperature and by heating and refluxing the system for 1 hour. Examples of bases may be caustic alkalis such as sodium hydroxide, potassium hydroxide, as well as organic amines, alkali carbonate, ammonia and quaternary ammonium hydroxide. Examples of organic compounds to be used are methanol, ethanol and acetone.

(4) Decomposition with alcohol containing acid catalyst:

It is further possible to transform an ozone-oxidized product directly into diesters of the ketodicarboxylic acid by the decomposition using an acid catalyst and alcohol. That is, esters of ketodicarboxylic acid are prepared by adding an alcohol containing catalytic amount of strong acids such as p-toluenesulfonic acid and sulfuric acid to the ozone-oxidation reaction liquid, followed by heating and refluxing for several hours. Examples of alcohol used here may be lower aliphatic alcohols, such as methanol, ethanol, isopropyl alcohol, butanol.

Yields of the ketodicarboxylic acids (No. 1, 2, 3, 4, 5, 6 and 7) or esters thereof (No. 8, 9) obtained through the aforementioned decomposition methods are tabulated in Table I below.

Table I

| No. | Decomposing agent | Yield |
|---|---|---|
| 1 | 1. peracetic acid, and<br>2. potassium hydroxide-water-methanol | 78% |
| 2 | 30% hydrogen peroxide | 52% |
| 3 | sodium sulfite aqueous solution | 40% |
| 4 | 1. triphenylphosphine, and<br>2. potassium hydroxide-water-methanol | 90% |
| 5 | 1. dimethyl sulfide, and<br>2. potassium hydroxide-water-methanol | 80% |
| 6 | sodium hydroxide-water | 20% |
| 7 | potassium hydroxide-methanol-water | 93% |
| 8 | sulfuric acid-methanol | 75% |
| 9 | p-toluenesulfonic acid-methanol | 73% |

Then, the decomposition of the ozonide of the compound II to form 4-oxopentadecanedionic acid IV will be below mentioned.

This decomposition process includes cleavage of ozonide, re-oxidation and decarboxylation and it is preferred to comprise reductive cleavage of the ozone-oxidized product with an inorganic reducing agent, subsequent re-oxidation, decomposition of excess oxidant and decarboxylation. All methods as referred to in the cleavage of the ozone-oxidized product of the compound I can be applied to the product derived from the compound II, but the reductive cleavage is preferred with regard to obtaining a high yield of the object and a low yield of by-products. For instance, when a peracid or a mixture of hydrogen peroxide and a lower carboxylic acid is employed for the oxidative cleavage, the final decomposition product obtained through re-oxidation and decarboxylation includes a large amount of compounds having aldehyde groups. When an acid or base aqueous solution is employed for hydrolysis, the final decomposition product obtained through re-oxidation and decarboxylation includes much dodecanedioic acid. Those methods give 4-oxopentadecanedioic acid IV at a low yield. In addition, when acetaldehyde is employed for the reductive cleavage, the final product obtained through re-oxidation and decarboxylation includes by-products having aldehyde groups. Employment of manganese acetate gives much by-product dodecanedioic acid. On the other hand, when sodium sulfite or sodium bisulfite is employed as a reducing agent, the final decomposition product includes only a small amount of dodecanedioic acid and compounds having aldehyde groups as by-product. It can be said that they are preferred as a reducing agent.

Below is mentioned the reductive cleavage of the ozone-oxidized product with sodium bisulfite. An amount of sodium bisulfite is preferred to be about 1.2 time equivalent weight of the compound II. Sodium bisulfite is added dropwise to the ozone-oxidized product maintained at −20° C. in the form of about 10 to 30 weight percent aqueous solution. This reaction is very exothermic and the temperature of the reaction system is immediately elevated up to room temperature. The reaction mixture is stirred at the elevated temperature for two hours. Then it is kept in the acidic condition with hydrochloric acid and is concentrated.

The concentrated mixture includes aldehyde group-containing compounds which are then re-oxidized with a peracid or a peroxide comprising hydrogen peroxide and a lower carboxylic acid in order to give the compound X. For instance, the re-oxidation is carried out by adding 30 to 35 percent hydrogen peroxide solution in 2 to 4 times equivalent weight of the compound II and formic acid or acetic acid in 5 to 10 times equivalent weight thereof and continuing the reaction at 40° C or lower, preferably 20° C, for 4 to 6 hours. If the re-oxidation is omitted, products having a higher boiling point are produced in a large amount and the yield of the keto-dicarboxylic acid IV is lowered. After the reaction, saturated aqueous solution of sodium bisulfite is added to the reaction product in order to decompose excess hydrogen peroxide or peracid for safety. Then the compound X is extracted with an organic solvent such as ether and benzene. The solvent is removed to obtain a crude intermediate containing the compound X having the formula:

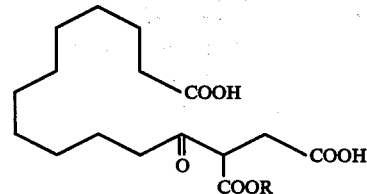

This compound X is subject to hydrolysis and decarboxylation by treatment with an alkali and then heated under the acidic condition. But the compound X having tertiary butyl group for R can be decarboxylated in the acidic condition only such as with heating and refluxing it in the hydrochloric acid aqueous solution to produce the precipitate of the decomposition product. Crude 4-oxo-pentadecanedioic acid IV is obtained by filtration or centrifugal separation after cooling the precipitate. There can be obtained diester of 4-oxo-pentadecanedioic acid having a high purity by esterification with a lower alcohol and distillation in vacuum.

4-oxo-pentadecanedioic acid IV is obtainable at the yield of 66.2% based on the moles of cyclododecanone through the referential examples 1 and 2 and Example 1 as mentioned later. Alternatively, the compound IV is obtainable at the yield of 60.8% based on the moles of cyclododecanone through Examples 5 and 7. Further combined with the Referential Example 3, the overall yields of cyclopentadecanone from cyclododecanone are 39.7% and 36.4%, respectively. This fact shows that this invention provides increased yield as another improved advantage in addition to the before-mentioned advantage of avoiding employment of polyphosphoric acid for conversion to ketone.

A process for preparing the compound II of this invention selectively will be described hereinafter.

There is the well known Stobbe reaction in which a diester of succinic acid and a ketone are condensed in the presence of a basic condensing agent to produce a half ester of an unsaturated dicarboxylic acid.

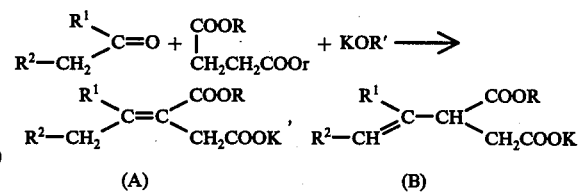

In the reaction, two products are obtainable, the alkenyl type compound of which corresponds to the compound II according to this invention. Accordingly the selectivity of this reaction must be noted herein. A reaction employing cyclododecanone as ketone is disclosed in Japanese patent publication 4341/69, which further describes both types of half esters as obtainable products, but it teaches nothing about their proportion. U.S. Pat. No. 3,778,483 discloses, in line 45 to 50 of 3 column, a chemical formula corresponding to the B type, but it has no detailed disclosure concerning the selectivity of the B type compound. It cannot be understood whether that compound could be obtained together with the A type compound. According to Biemann et al, J. Am. Chem. Soc. 79, 5558 (1957), cyclododecanone and diethyl succinate are condensed to give alkylidene type compound III, that is A type, which is identified with UV spectrum.

We have studied the prior art and have made further researches, so that we have found that the reaction between di-alkyl succinate and cyclododecanone gives the alkenyl type compound II with selectivity. In the reaction of this invention, solvents to be used includes conventional ones such as tert-butyl alcohol, tetrahydrofuran and benzene. As a condensing agent, there may be used tert-BuOK, $NaNH_2$, NaH and $NaOC_2H_5$. When a condensing agent other than an alkali alcoholate and an aprotic solvent are used, it is necessary to add a small amount of alcohol as an initiator. The di-alkyl succinate to be used in this invention includes di-tert-butyl succinate, di-sec-butyl succinate and di-isopropyl succinate. This reaction advantageously suppresses by-production of the compound XII having the formula:

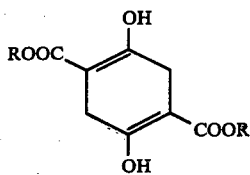

which can result from self-condensation, by means of employment of di-alkyl succinate. Accordingly it is reasonable that di-alkyl succinate is generally used in about equivalent mole of cyclododecanone. But an excess amount thereof results in an increased yield. A basic agent can be also used in about a molar equivalent to the cyclododecanone, but an excess amount thereof results in increased yield. The process according to this invention comprises either adding a mixture of cyclododecanone, di-alkyl succinate and optionally a solvent dropwise to a solvent including a condensing agent, or adding cyclododecanone previously thereto and then adding di-alkyl succinate. The addition and the reaction are carried out at a reflux temperature of the solvent used. According to this invention, the condensation reaction takes place rather quickly, for instance from 30 minutes to 4 hours after the addition step carried out over 10 minutes to 1 hour. The reaction time in the continuous reaction is considered to be an average residence time. Too long reaction time will result in undesired by-production. After the condensation, the reaction product is neutralized with an acid such as hydrochloric acid and if necessary concentrated, followed by extraction of the condensation product II with an organic solvent. Benzene can be used as the reaction solvent and the extraction solvent. In case a water-soluble solvent such as t-butyl alcohol and tetrahydrofuran is used for the reaction, the solvent is removed with distillation and the reaction product is extracted with another extraction solvent such as toluene, chloroform and ether. Crude crystals of the product can be obtained by concentration of the extraction liquid. The crude crystals are subjected to various analyses, or the extraction liquid in chloroform is transferred as it is to the ozone oxidation. It was established from the results of analysis of N.M.R. and gas chromatography that the alkenyl type compound II could be obtained with very high selectivity. More detailed disclosure will be shown in Example 5.

Examples of the present invention are illustrated below.

EXAMPLE 1: (conversion of I to IV)

10 Grams of 13-oxabicyclo [10.4.0] hexadec-1(12)-en-14-one I was dissolved in 150 ml of a chloroform, and to which was blown oxygen containing about 5% of ozone by cooling the system to −20° C. When the reaction got a blue color of ozone dissolved therein, the reaction system was purged with nitrogen, and to which was dropwisely added 40 ml of a solution consisting of 70% of methanol and 30% water in which has been dissolved a potassium hydroxide in an amount of about 30% by weight, by maintaining the temperature of the system at −20° C. The reaction temperature was returned back to room temperature while the stirring was continued, and then the system was refluxed for 2 hours and condensed. The condensed residue was dissolved by the addition of water and rendered to be acidic with concentrated hydrochloric acid; crystals began to precipitate. The crystals were separated by filtration and washed with a chloroform to obtain 11.28 g (yield 93%) of 4-oxopentadecanedioic acid IV in almost pure form.

Melting Point: 117° to 118° C    IR 1700 $cm^{-1}$
(Absorption based on C=O bondage)

The compound was also confirmed by a mass spectrum parent peak m/e 314 of dimethyl ester.

EXAMPLE 2: (conversion of I to IV)

10 Grams of the compound I was oxidized with ozone under the same conditions as in Example 1, and to which were added 25% by weight of a peracetic acid and 20 ml of an ethyl acetate solution. The mixture was left to stand at room temperature overnight and condensed, and to which were added excess amount of potassium hydroxide and a solution of water and methanol; the mixture was heated and refluxed. The reaction mixture was condensed, and to the condensed residue was added water and then rendered to be acidic with concentrated hydrochloric acid; crystals were precipitated. The crystals were separated by filtration and washed with chloroform to obtain 9.45 g of ketodicarboxylic acid IV.

EXAMPLE 3: (conversion I to IV)

10 Grams of the compound I was oxidized with ozone under the same conditions as in Example 1, and to which was added 20 ml of a chloroform in which is dissolved 16.6 g of a triphenyl phosphine, and the temperature was returned back to room temperature with stirring. The reaction liquid was condensed, and to the residue was added water-methanol solution of potassium hydroxide, followed by the treatment in the same manner as in Example 2 to obtain 10.91 g of ketodicarboxylic acid IV.

EXAMPLE 4: (Conversion of I to dimethyl ester of IV)

10 Grams of the compound I was oxidized with ozone under the same conditions as in Example 1, and to which was dropwisely added 50 ml of methanol containing 1 g of a sulfuric acid. The temperature was then returned back to room temperature with stirring, and the system was left to stand for 4 hours, and then heated and refluxed for 4 hours. The reaction liquid was condensed, and the condensate was dissolved in ether, washed with an aqueous solution of a sodium hydrogencarbonate and then with water. After dried, the mixture was condensed and distilled off under vacuum condition to obtain a dimethyl ester of a ketodicarboxylic acid IV.

Yield 9.88 g (75%), b.p. 155° to 160° C/0.3 mmHg

EXAMPLE 5: (conversion of VIII to II)

20.06 Grams (0.418 mole) of 50% sodium hydride dispersion was introduced into a 1 liter four-necked flask equipped with a thermometer, a tap funnel, a reflux cooler and a stirrer and washed with benzene. Then 500 ml of pure tetrahydrofuran and 20 ml of t-BuOH were added thereto and the mixture was refluxed for 30 mins. During the reflux, there was dropwise added 150 ml of pure tetrahydrofuran containing dissolved therein 61.87 g (0.340 mol) of cyclododecanone and 86.0 g (0.374 mol) of di-tert-butyl succinate, over 1.5 hour. After that the reflux was continued to complete the reaction. After the reaction, a mixture of 100 ml of water and 78 ml of concentrated hydrochloric acid was added to the reaction product and the obtained mixture was concentrated. The solvent was removed and the product mixture was twice extracted with 250 ml of ether. The extract liquid was washed with water and dried, followed by concentration to obtain 115.1 g of crude $\beta$-cyclododecenyl-$\beta$-tert-butoxycarbonyl propionic acid II with the purity of 86.8% and the yield of 86.9%. The crude product was found to include about 2% of cyclododecanone and about 5% of high boiling point-having by-products and the balance of the impurities was solvents.

Figure 2:
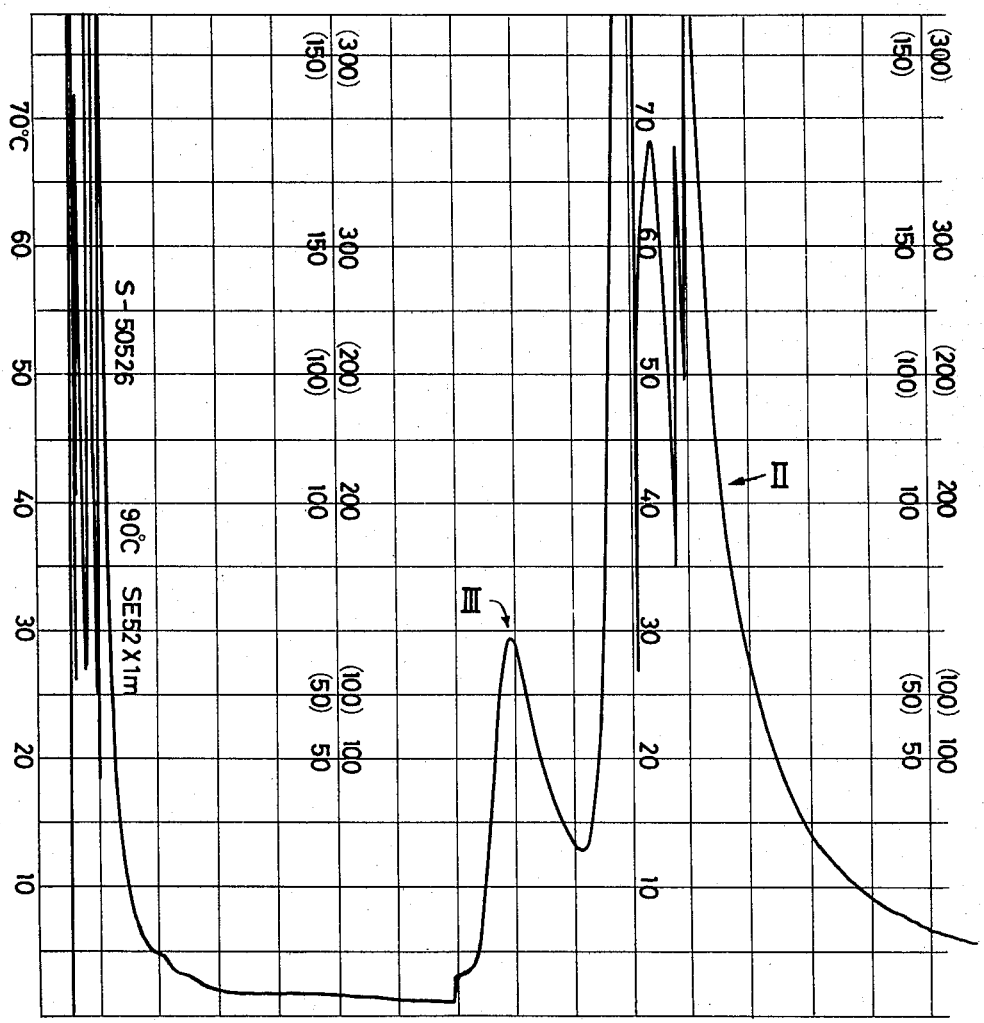

Two kinds of half methyl esters were analyzed as follows. The NMR spectrum of the methyl ester of the compound II is like FIG. 1B and that of the compound III is like FIG. IA. The measurement was carried out in $CCl_4$. These methyl derivatives of the compounds II and III could be distinguished from each other also with gas chromatogram, which is shown in FIG. 2. It is understood from the results of the analysis that $\beta$-cyclododecylidene-$\beta$-tert-butoxycarbonylpropionic acid III was contained in the reaction product in a very small amount.

Another experiment was carried out as follows. 84.4 g (0.418 mol) of di-isopropyl succinate replaced for di-tert-butyl succinate, the same amount of isopropanol replaced for tert-butanol and 34.6 g (0.19 mol) of cyclododecanone were employed and the other reaction conditions were the same as mentioned above. The obtained product was analyzed with results that $\beta$-cyclododecylidene-$\beta$-isopropoxycarbonylpropionic acid III was not included therein and that $\beta$-cyclododecenyl-$\beta$-isopropoxylcarbonyl propionic acid II was selectively obtained.

EXAMPLE 6: (conversion of VIII to II)

Di-tert-butyl succinate XI and cyclododecanone VIII were condensed in the same manner as in Example 5 employing various condensing agents, solvents and initiators. The reaction conditions and the results are shown in Table 1.

Table 1

| Condensing agent | Solvent | Initiator | Molar Ratio XI/VIII | Molar Ratio condensing agent/VIII | Dropping time min. | Temp. | Reaction time hours | Product Yield of II % | By-product |
|---|---|---|---|---|---|---|---|---|---|
| NaH | t-BuOH | — | 1.0 | 2.2 | 8 | reflux | 4 | 81.0 | |
| NaH | benzene | t-BuOH | 1.0 | 1.1 | 30 | reflux | 4 | 69.2 | |
| NaH | THF | t-BuOH | 1.0 | 1.1 | 30 | reflux | 4 | 80.3 | III and |
| NaNH$_2$ | THF | t-BuOH | 1.2 | 1.2 | 30 | reflux | 4 | 90.1 | XII were |
| NaNH$_2$ | THF | t-BuOH | 1.2 | 1.2 | 30 | 50° | 4 | 78.0 | little |
| NaOCH$_3$ | t-BuOH | — | 1.0 | 1.3 | 30 | reflux | 4 | 62.9 | produced. |
| t-BuOK | t-BuOH | — | 1.0 | 2.4 | 30 | reflux | 2 | 86.5 | |

For comparison, diethyl succinate and cyclododecanone were condensed in t-BuOH in the presence of t-BuOk at a normal temperature for 17 hours, so that two half esters, corresponding to II and III, were obtained at the ratio of 4 : 6. Separately, the same starting materials were reacted at 60° C for 30 minutes after dropping a reactant over 30 mins., when a large amount of 2,5-dihydroxycyclohexa-1,4-dien-1,4-dicarboxylic acid diethyl ester XII was found as by-product in addition to the compound II.

EXAMPLE 7: (conversion of II to IV)

93.03 g (0.25 mol) of $\beta$-cyclododecenyl-$\beta$-tert-butoxy-propionic acid II obtained in Example 5, 90 g of acetic acid and 400 g of chloroform were introduced into a three-necked flask and maintained at $-20°$ C. Then oxygen gas containing ozone was blown therein and the end point of the reaction was considered when the reaction mixture turned light blue. After the reaction, the reaction system was substituted by nitrogen gas and aqueous solution of sodium bisulfite was added in 1.2 time equivalent weight of the starting half ester II to the reaction mixture maintained at $-20°$ C and stirred. The reaction was exothermic and the reaction mixture reached a room temperature, at the same temperature the reaction was continued for further two hours. Then hydrochloric acid aqueous solution was added to make acidic and the reaction product was concentrated. To the condensate were added 68 g of formic acid and 134 g of hydrogen peroxide liquid and the mixture was allowed to stand at 20° C for 6 hours. Then aqueous solution of sodium bisulfite was added thereto to decompose excess hydrogen peroxide. The product was extracted with ether and the ether layer was concentrated. Furthermore, the concentrated product was mixed with 100 ml of concentrated hydrochloric acid and the mixture was refluxed for 5 hours. After cooling, 76.2 g of crude crystals were obtained with filtration and drying. The crude product was further esterified by diazomethane to dimethyl ester, which was analyzed with internal standard method of gas chromatography. The result is 65.9% of 4-oxopentadecanedioic acid, 2.4% of cyclododecanone and 2.3% of dodecanedioic acid. The yield of 4-oxo-pentadecanedioic acid was 70% based on the compound II. The crude compound IV was purified with esterification with methanol and distillation under vacuum. Boiling point of dimethyl ester of IV: 158° to 180° /0.55 mmHg.

EXAMPLE 8: (conversion of II to IV)

The compound II was ozone-oxidized in the same manner as Example 7 except for conditions of solvent, re-oxidation and decarboxylation and then the product was decomposed to produce the compound IV. The reaction conditions and results are shown in Table 2.

Table 2

| Common conditions | fatty acid | $H_2O_2$ | re-oxidation formic acid | temp. | hour | Yield of compound IV | Yield of dodecanedioic acid as by-products |
|---|---|---|---|---|---|---|---|
| ozone oxidation II (R:t-Bu) 20 g chloroform 80 g −20° C 4 hours reduction $NaHSO_3$ in 1.2 time equivalent is divided into two portions. decarboxylation 10 ml of HCl, 10 ml of water reflux for 3 hours. | acetic acid | 5 mol per the compound II | 2 | 5 | 20 | 4 | 64.9% | 1.4 |
| | " | " | 4 | 10 | 40 | 3 | 70.1 | 4.3 |
| | formic acid | " | 2 | 10 | 20 | 6 | 45.0 | 4.5 |
| | | | re-ocidation | decarboxylation | | | | |
| ozone oxidation II (R:t-Bu) 10 g Chloroform 90 g −20° C until colored (about 1.8 hour) reduction 1.2 time equivalent weight without division re-oxidation $H_2O_2$ and formic acid in 2 equivalent weight of the compound II and 5, respectively. 20° C, 2 hours. | acetic acid | 10 | carried out | HCl | 2.4 | $H_2O$ 20 ml | 63.1 | 7.7 |
| | " | 5 | not | NaOH | 2.4 | $H_2O$ 10 ml | 23.5 | 5.0 |
| | " | 10 | carried out | NaOH | 1.2 | $H_2O$ 20 ml | 51.6 | 2.4 |

REFERENCE EXAMPLE 1: (conversion of VIII to IX)

Cyclododecanone and diethyl carbonate were allowed to react in the presence of a base to give 2-ethoxycarbonylcyclododecanone in 93% yield. Ten grams of the 2-ethoxycarbonylcyclododecanone was dissolved in 40 ml of toluene and the resulting solution was added dropwise into a solution of 2.4 g of sodium hydride (purity 60%) suspended in toluene and kept at 80° C. After the completion of the dropping, the solution thus obtained was stirred for 30 minutes and then the reaction temperature was cooled to room temperature. Thereafter, into the solution was dropped 5.7 g of β-propiolactone and further 25 ml of aqueous sodium hydroxide solution was added, and was refluxed for 4 hour. After the reaction was complete, the aqueous layer of the solution was drawn off and acidified with hydrochloric acid to give 8.5 g of β-(2-oxocyclododecyl)propionic acid as white crystals. The product melts at 101° to 102° C.

REFERENCE EXAMPLE 2: (conversion of IX to I)

β-(2-oxocyclododecyl)propionic acid (8.0 g) was dissolved in a mixed solution of 400 ml of ethyl acetate, 80 ml of acetic anhydride, and 0.01 ml of 75% perchloric acid and stirred at a temperature of 15° to 20° C for 3.5 hours. After the completion of the reaction, the resulting reaction solution was washed with 50 ml of 5% aqueous sodium bicarbonate solution, and further washed with saturated aqueous sodium chloride solution, and then dried by adding Glauber's salt (sodium sulfate) and finally filtered. Thereafter, the ethyl acetate, acetic acid and acetic anhydride in the filtrate were distilled off under reduced pressure and the resulting residue was distilled to give 6.7 g of the compound of formula (I), which was 90% of theoretical yield. The structure of the compound was identified by using IR, Mass and N.M.R. spectra data and elementary analysis data.

REFERENCE EXAMPLE 3: (conversion of IV to VI)

Five grams of 4-oxopentadecanedioic acid obtained in Examples and 2.2 g of potassium hydroxide were dissolved in 40 ml of ethylene glycol, 12 ml of hydrazine hydrate was added and the mixture was refluxed for 8 hours. Then, 7.2 g of potassium hydroxide was added to the mixture and the mixture was heated for 6 hours. The reaction solution was poured into water and acidified with concentrated hydrochloric acid to give a precipitate, which was esterified with methanol an distilled off at 130° to 131° C/0.1 mmHg, thus obtaining 4.2 g of the compound: dimethyl pentadecanedioate in 80% yield.

The latter compound could be transformed to cyclopentadecanone in 75% yield by the general method of acyloin condensation and reduction.

What we claim is:

1. A process for preparing 4-oxopentadecanedioic acid which comprises: oxidizing, with ozone, at a temperature of from −80° C to room temperature, a compound having the formula:

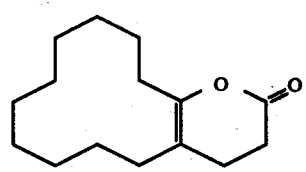

said compound being dissolved in an inert organic solvent, to transform said compound to the corresponding ozonide; then adding to the reaction mixture containing said ozonide a basic aqueous solution of a base selected from the group consisting of sodium hydroxide, potassium hydroxide, organic amines, alkali carbonates, ammonia and ammonium hydroxide and a water-soluble organic compound selected from the group consisting of methanol, ethanol and acetone, at from −30° to 0° C, then heating the mixture at reflux to decompose said ozonide and then hydrolyzing to obtain 4-oxopentadecanedioic acid.

2. A process for preparing diester of 4-oxopentadecanedioic acid which comprises: oxidizing, with ozone, at a temperature of from −80° C to room temperature, a compound having the formula:

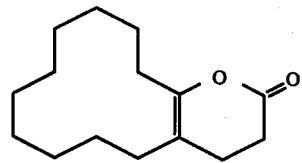

said compound being dissolved in an inert organic solvent, to transform said compound to the corresponding ozonide; then adding to the reaction mixture containing said ozanide an alcohol selected from the group consisting of methanol, ethanol, isopropyl alcohol and butanol, said alcohol containing a catalytic amount of a strong acid selected from the group consisting of p-toluene sulfonic acid and sulfuric acid, and refluxing the mixture to transform said ozonide to the corresponding diester of 4-oxopentadecanedioic acid.

* * * * *